United States Patent [19]

Loh

[11] Patent Number: 5,236,563
[45] Date of Patent: Aug. 17, 1993

[54] SURFACE-MODIFIED BIOABSORBABLES

[75] Inventor: Inh-Houng Loh, Maynard, Mass.

[73] Assignee: Advanced Surface Technology Inc., North Billerica, Mass.

[21] Appl. No.: 540,118

[22] Filed: Jun. 18, 1990

[51] Int. Cl.$^5$ .............................................. A61F 2/00
[52] U.S. Cl. ............................ 204/165; 606/230; 606/231; 424/426
[58] Field of Search ............... 204/165, 168, 169; 424/426, 78; 606/230, 231; 623/901

[56] References Cited

U.S. PATENT DOCUMENTS

| | | | |
|---|---|---|---|
| 3,700,489 | 10/1972 | Borysko | 606/230 |
| 4,718,907 | 1/1988 | Karwoski et al. | 204/169 |
| 4,764,364 | 8/1988 | Heller | 424/78 |
| 4,891,225 | 1/1990 | Langer et al. | 424/428 |
| 4,904,260 | 2/1990 | Ray et al. | 623/17 |

FOREIGN PATENT DOCUMENTS

| | | | |
|---|---|---|---|
| 130814 | 2/1946 | Australia | 606/231 |
| 586635 | 11/1959 | Canada | 606/230 |
| 2120694 | 12/1983 | United Kingdom | 204/165 |

*Primary Examiner*—John Niebling
*Assistant Examiner*—Arun S. Phasge
*Attorney, Agent, or Firm*—Schiller & Kusmer

[57] ABSTRACT

A bioabsorbable synthetic polymer is exposed to a gas plasma in a chamber at a pressure substantially below atmospheric for a sufficient time to increase the hydrophobicity and/or cross-linking density of a surface layer thereof and thereby modify the rate at which the polymer will hydrolyze. An accordingly modified polymer is useful for surgical implants and wound closures.

16 Claims, 1 Drawing Sheet

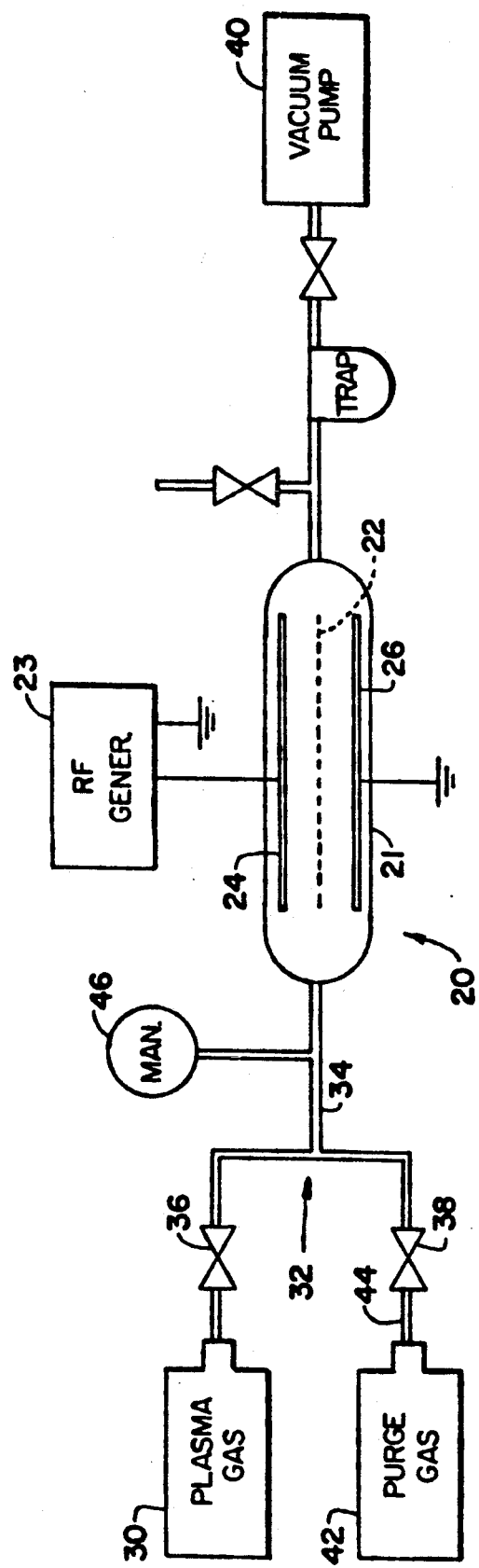

SURFACE-MODIFIED BIOABSORBABLES

This invention relates to bioabsorbable materials, and more particularly to surgical implant and wound closure materials made from synthetic polymers capable of being absorbed in the body of an animal or person.

Surgical implants for the reconstruction of injured, diseased, or aged human bodies have become an increasingly important aspect of modern reconstructive surgery, because these polymers eventually degrade and leave no trace of foreign materials inside the human body for prolonged chronic foreign body reactions. However, the lack of synchronization between the degradation property of synthetic absorbable polymers and the healing rate of the tissues to be replaced or repaired, limits their application and acceptance. This is particularly true with respect to synthetic absorbable polymers used to close wounds in more demanding situations (orthopedic and cardiovascular applications), or where wound healing may be delayed because of diseases such as cancer, AIDS, diabetes, or therapeutic treatments such as organ transplantation and chemotherapy.

The current use of synthetic absorbable polymers as implants for orthopedics, cardiovascular surgery, body-wall reinforcement, urology, gastrointestinal surgery, nerve repair, controlled drug release and dentistry is largely experimental. For example, degradable linear aliphatic polyesters have been molded as bone plates and screws for the internal fixation of injured bone or as the fillers for defective bone. The main obstacle to such use of synthetic absorbable polymers is the difficulty of achieving an adequate degradation rate so that the absorbable prosthesis can maintain suitable mechanical properties for at least four months, allowing adequate mineralization of bone callus.

The most common and frequent present use of the synthetic absorbable polymers is as surgical sutures to close wounds. Catgut, made of collagen and derived from sheep intestinal submucosa, is probably the first absorbable suture material. Not until the late 1960's were synthetic absorbable polymers made into fibers that, when placed in living tissues, would degrade into subunits that could then be phagocytosed by macrophages. Currently available synthetic absorbable suture materials are typified by polyglycolic acid sold under the trademark "DEXON" by the Davis and Geck Division of American Cyanamid Co., polyglycolide-co-lactide sold under the trademark "VICRYL" and available from the Ethicon division of Johnson & Johnson Co., poly(p-dioxanone) sold under the trademark "PDS" by Ethicon, and polyglycolide-co-trimethylene carbonate sold under the trademark "MAXON" by Davis and Geck.

The use of such commercially available materials as absorbable sutures has been satisfactory in a variety of animal and human tissues, but when used in the more demanding situations like orthopedics, cardiovascular, and abdominal surgery, there are still problems.

Although nonabsorbable polypropylene type sutures are considered to be the standard choice in cardiovascular surgery, the use of synthetic absorbable sutures has become increasingly popular, particularly for use in children. However, the major concern when using synthetic absorbable sutures in vascular anastomosis is the unequal degradation rate of the suture to the healing rate of the vascular tissue. If the suture degrades too rapidly before anastomosis achieves adequate strength, disruptions, leakage and false aneurysms can be major complications.

The current commercially available synthetic absorbable polymeric sutures tend to lose their tensile strength through hydrolytic degradation when exposed to water in the tissues. Recently, it was found that these synthetic absorbable polymeric sutures lost their tensile strength faster when they were slightly elongated during use. There is also a suspicion that certain enzymes and bacteria are able to influence the rate of hydrolysis of absorbable suture materials under appropriate conditions.

The principal object of the present invention is to provide synthetic absorbable polymers in which the degradation rate is controllable. Other objects of the present invention are to provide such polymers which have been surface treated to alter their surface cross-links and/or hydrophobicity, and particularly such characteristics as wettability and fluid diffusivity, so as to modulate the hydrolyzation rate of such polymer; to provide such surface treatment by exposing said polymer to a selected low-temperature gas plasma at a pressure substantially below atmospheric for a sufficient time to increase the hydrophobicity thereof; and to provide a method for plasma treating synthetic absorbable polymers to confer desirable degradation characteristics on the polymers.

Other objects of the present invention will in part be obvious and will in part appear hereinafter. The invention accordingly comprises the method comprising the several steps and the relation of one or more of such steps with respect to each of the others, and the product possessing the features, properties and relation of components, all of which are exemplified in the following detailed disclosure and the scope of the application of which will be indicated in the claims.

For a fuller understanding of the nature and objects of the present invention, reference should be had to the following drawing wherein there is shown a schematic diagram of apparatus for surface modifying polyglycolic and polylactic type synthetic absorbable polymers by plasma treatment.

The foregoing and other objects of the present invention are achieved through the provision of synthetic absorbable polymers having their surface layers modified to alter the hydrolytic degradation of the bioabsorbable materials (the main mechanism of their biodegradation), the modification being effected by exposure to selected low-temperature gas-plasma so as to add to the cross-links in a thin surface layer of the polymer and/or to increase the surface hydrophobicity of the polymer by reacting the surface thereof with surface-nmodifying components, typically halogens such as fluoride ions.

Degradation of synthetic absorbable polymers inside the human body or in a simulated biological environment is believed to be due to hydrolytic and/or enzyme catalyzed hydrolytic cleavage of hydrolyzable bonds. Thus, it is postulated that the degradation of synthetic absorbable polymers can be controlled by controlling the rate of water permeation into them. It is believed that surface modifications of the polymer which can retard the diffusion and solubility of water and/or enzyme molecules into the material will slow the hydrolytic degradation process acting on the polymer. Thus, in the present invention, the surface layer of synthetic absorbable polymer is modified by exposure to a low-temperature gas plasma so as to regulate the hydrophobicity and therefore the rate at which tensile strength loss of the polymer occurs when implanted in a body. Such surface modification changes the water wettability and solubility characteristic of the synthetic absorbable polymer by creating a hydrophobic surface, and cross-links the outermost layers of the polymers thereby decreasing the diffusivity of water molecules in this region.

Specifically, the present invention lies in the method of treating a bioabsorbable synthetic polymer to modify or modulate the hydrolyzation rate of such polymer, i.e., the rate at which such polymer will degrade by hydrolysis in the presence of water, particularly when implanted in a living body. The method of the present invention thus comprises the step of exposing the polymer to a gas plasma in a chamber at a pressure substantially below atmospheric for a sufficient time to increase the hydrophobicity and/or the cross-linking density of a surface layer thereof without substantially reducing the tensile strength of the polymer. Preferably, the surface treatment is limited in time to be sufficient to treat the surface layer to a depth between about 100 to 1500 Angstroms, thereby producing a cross-linked polymer layer that will not materially adversely affect the desired handling qualities of the polymer, for example, when the latter is in the form of a suture material.

It is known that exposure of polymers to a discharged inert gas plasma may result in extensive cross-linking at or adjacent the polymer surface. Both the ultraviolet radiation and reactive radicals in the plasma are capable of generating free radicals on the surfaces of many polymers which lead to the formation of cross-links at the outermost surface. In the present invention, this cross-linked layer is believed to slow the passage of small molecules through the surface layers of the treated polymer resulting in the reduction of hydrolytic degradation rate during the critical period of wound healing. The development of such a surface cross-linked layer has been shown to be related to the length of exposure to the plasma, the choice of the plasma conditions, and the nature of the polymer. It is also known that this cross-linked surface layer can constitute a hydrophobic surface. For example, Loh et al., report a significant reduction in solvent transmission through plasma fluorinated polymer films (*Poly. Mater. Sci. and Eng.*, 56, 227, 1987; *Poly. Eng. and Sci.*, 27(11), 861, 1987).

Among the biodegradable polymers suitable for treatment according to the process of the present invention are polyglycolic acid, polylactic acid, polyglycolide-lactide copolymers, polydioxanones, poly(glycolide-co-trimethylene carbonates), polyethylene carbonates, polyiminocarbonates, poly-$\beta$-hydroxybutyrates, polyester-amides, polyorthoesters, polyanhydrides, cyanoacrylates, and the like.

BRIEF DESCRIPTION OF THE DRAWINGS

Apparatus 20 used for plasma surface modification in accordance with the principles of the present invention, as shown in FIG. 1, includes quartz bell-jar type reactor chamber 21 (e.g., 12" diameter, 18" height) where the reaction between the synthetic absorbable polymeric surface and the plasma occurs.

DETAILED DESCRIPTION

Positioned in chamber 21 are rack 22, preferably made of stainless steel and a pair of parallel electrode plates 24 and 26 (e.g., 7"×7"×¼" aluminum plates) between which the plasma is formed. Radio frequency generator 23 is provided as a source of potential, the output terminal of generator 23 being connected to plate 24, plate 26 being grounded, thereby providing means for generating an electrical field between the plates, in which field a plasma can be created and sustained. To provide the desired gas from which the plasma is formed, the apparatus includes gas source 30 (typically a standard gas cylinder) connected through gas inlet system 32 to chamber 21. System 32 is typically formed of supply line 34 connected to source 30, valve 36 for controlling the flow of gas through line 34, and valve 38. The apparatus also includes vacuum pump 40 connected to chamber 21 for reducing the gas pressure therein. A source 42 of purge gas such as helium is connected through line 44 to valve 38 of valve system 32.

In a typical reaction, synthetic absorbable polymeric sutures are mounted in chamber 21 on steel rack 22, the latter then being positioned between electrodes 24 and 26. Vacuum pump 40 is operated to reduce the pressure in chamber 21 to below 0.1 torr. Valve system 32 is operated to permit reacting gas monomer from source 30 to flow into chamber 21 through line 34 for approximately 10 minutes before generating a plasma.

The plasma is created by applying the output of radio frequency generator 23, operating typically at 13.56 MHz, to electrode plate 24. The power supplied by generator 23 is controlled at the minimum required to sustain the plasma, generally 50 to 100 watts. Higher powered plasma will only degrade the surface of the polymers. The reaction between the plasma and the synthetic absorbable polymer surface is allowed to proceed for a period of time determined by the desired thickness and surface energy on the substrates and the concentration of gas monomers in the reacting vapor. Typical reaction times are 3 minutes to 60 minutes. The thickness of the treated surface layer of the polymer should be between about 100 to 1500 Angstroms, preferably between about 200 and 1000 Angstroms. The pressure in chamber 21, as measured by capacitance nanometers 46 coupled to chamber 21 is maintained at 50 millitorrs throughout the reaction period.

Finally, all flow of gas from source 30 is terminated, the power from generator 23 sustaining the plasma is turned off, and valve 38 is opened to permit purge gas to flow into chamber 21 from source 42 to purge the suture surface of highly reactive radicals which could cause premature contamination of the surface. Valve 38 is then closed, the door to reactor chamber 21 is opened so that chamber 21 is returned to atmospheric pressure, and the surface modified synthetic absorbable polymeric is removed.

As gases from which the plasma is created, it is preferred to use inert gases such as the noble gases, and those containing compounds of carbon, silicon and/or fluorine or combinations thereof, but other gases, such as those containing other surface modifiers, are also useful. Examples of suitable gases are argon, methane ($CH_4$), trimethylsilane (TMS), tetrafluoroethylene (TFE), and the like. The use of $CH_4$ plasma to treat a synthetic absorbable polymer created a surface cross-linked hydrocarbon layer; TFE plasma provided a hydrophobic cross-linked surface (the chemical structure of which is believed to be similar to a perfluorinated hydrocarbon such as polytetrafluoroethylene); TMS plasma generated a Si-containing hydrocarbon surface. It is important to emphasize that the plasma surface treatment causes modification of the existing surface by reacting the near-surface units of the polymer chain molecules with reactive species. Delamination, cracking, or crazing, which occur with conventional coatings, are and have not been observed on surfaces modified with this plasma process.

As shown in the following examples, a number of different synthetic absorbable polymers, in the form of sutures, were treated by various plasmas. Following treatment, the sutures were evaluated as described hereinafter.

EXAMPLE 1

Sutures made of polyglycolic acid and sold under the trademark "DEXON" by the Davis and Geck Division of American Cyanamid Co., were treated by exposure of the material as above described for 35 minutes to a $CH_4$ plasma at a flow rate of 2 sccm to achieve a deposition rate of 0.2 to 0.4 Å/sec. The thickness of surface layer treated was about 600Å.

EXAMPLE 2

"DEXON" sutures were treated by exposure of the material as described in Example 1 but for 60 minutes. The thickness of surface layer treated was about 1000Å.

EXAMPLE 3

"DEXON" sutures were treated by exposure of the material as above described for 5 minutes to a TFE plasma at a flow rate of 3.3 sccm to achieve a deposition rate of 2 to 2.3 Å/sec. The thickness of surface layer treated was about 600Å.

EXAMPLE 4

"DEXON" sutures were treated by exposure of the material as above described for 8 minutes to a TFE plasma at a flow rate of 3.3 sccm to achieve a deposition rate of 2 to 2.3 Å/sec. The thickness of surface layer treated was about 1000Å.

EXAMPLE 5

Sutures made of polyglycolide-co-lactide, sold under the trademark "VICRYL" and available from the Ethicon division of Johnson & Johnson Co., were treated by exposure of the material as above described for 35 minutes to a $CH_4$ plasma at a flow rate of 2 sccm to achieve a deposition rate of 0.2 to 0.4 Å/sec. The thickness of surface layer treated was about 600Å.

EXAMPLE 6

"VICRYL" sutures were treated by exposure of the material as described in Example 5 but for 60 minutes. The thickness of surface layer treated was about 1000Å.

EXAMPLE 7

"VICRYL" sutures were treated by exposure of the material as above described for 5 minutes to a TFE plasma at a flow rate of 3.3 sccm to achieve a deposition rate of 2 to 2.3 Å/sec. The thickness of surface layer treated was about 600Å.

EXAMPLE 8

"VICRYL" sutures were treated by exposure of the material as above described for 8 minutes to a TFE plasma at a flow rate of 3.3 sccm to achieve a deposition rate of 2 to 2.3 Å/sec. The thickness of surface layer treated was about 1000Å.

EXAMPLE 9

Sutures made of poly(p-dioxanone) and sold under the trademark "PDS" by the Ethicon division of Johnson & Johnson Co., were treated by exposure of the material as above described for 10 minutes to a $CH_4$ plasma at a flow rate of 2 sccm to achieve a deposition rate of 0.2 to 0.4 Å/sec. The thickness of surface layer treated was about 200Å.

EXAMPLE 10

"PDS" sutures were treated by exposure of the material as above described for 25 minutes at a flow rate of 2 sccm to a $CH_4$ plasma to achieve a deposition rate of about 0.2 to 0.4 Å/sec. The thickness of surface layer treated was about 400Å.

EXAMPLE 11

"PDS" sutures were treated by exposure of the material as above described for 3.5 minutes to a TFE plasma at a flow rate of 3.3 sccm to achieve a deposition rate of 2 to 2.3 Å/sec. The thickness of surface layer treated was about 400Å.

EXAMPLE 12

"PDS" sutures were treated by exposure of the material as above described for 8 minutes to a TFE plasma at a flow rate of 3.3 sccm to achieve a deposition rate of 2 to 2.3 Å/sec. The thickness of surface layer treated was about 1000Å.

EXAMPLE 13

Sutures made of polyglycolide-co-trimethylene carbonate and sold under the trademark "MAXON" by Davis and Geck, were treated by exposure of the material as above described for 10 minutes to a $CH_4$ plasma at a flow rate of 2 sccm to achieve a deposition rate of 0.2 to 0.4 Å/sec. The thickness of surface layer treated was about 200Å.

EXAMPLE 14

"MAXON" sutures were treated by exposure of the material as above described for 25 minutes at a flow rate of 2 sccm to a $CH_4$ plasma to achieve a deposition rate of about 0.2 to 0.4 Å/sec. The thickness of surface layer treated was about 400Å.

EXAMPLE 15

"MAXON" sutures were treated by exposure of the material as above described for 6 minutes to a TMS plasma at a flow rate of 2 sccm to achieve a deposition rate of 0.8 to 1.1 Å/sec. The thickness of surface layer treated was about 400Å.

EXAMPLE 16

"MAXON" sutures were treated by exposure of the material as above described for 15 minutes to a TMS plasma at a flow rate of 2 sccm to achieve a deposition rate of 0.8 to 1.1 Å/sec. The thickness of surface layer treated was about 1000Å.

Sutures made of selected synthetic absorbable polymers, surface treated in accordance with the present invention as described in the above Examples were evaluated in vitro as follows. The surface treated sutures were immersed in phosphate buffer baths up to 28 days at pH=7.44 and 37° C. Representative samples of the sutures were removed from the bath at the end of 42, 60, 90, 120, and 150 day periods. Samples of corresponding untreated synthetic absorbable polymer sutures served as controls for evaluating the merits of each of the surface treated sutures. At the end of each period, some representative samples were removed from the bath and tested for tensile breaking strength, weight loss, surface morphology, and dye diffusion under a controlled environment (65% RH, 21° C.). The unimmersed treated and untreated PDS and MAXON sutures were also examined for both hydrophobicity by wetting force and bending stiffness. DEXON and VICRYL sutures were not examined for hydrophobicity by wetting force because their braided geometry makes the analysis of wettability data extremely complex and difficult.

The experimental procedures for these tests are given in such publications as C. C. Chu, "Strain-Accelerated Hydrolytic Degradation of Synthetic Absorbable Sutures", *Surgical Research Recent Development*, C. W. Hall (Ed.), Pergamon Press, San Antonio, Tex. (1985); D. F. Williams and C. C. Chu, "The effect of enzymes and gamma irradiation on the tensile strength and morphology of PDS fibers", *J. Appl. Polymer Sci.*, 29, 1865, 1984; B. Miller, "Methodology for Studying the Wettability of Filaments", *Text. Res. J.*, 5, 359, 1975; C. C. Chu and Z. Kizil, "Quantitative Evaluation of Stiffness of Commercial Suture Materials", *Surg. Gynecol. & Obstet.*, 168, 233, 1989; and elsewhere.

The percentages of tensile breaking strength remaining of the plasma-surface treated synthetic absorbable sutures after periods in the bath were determined based on the corresponding untreated synthetic absorbable sutures controls. The improvement in tensile breaking strength of synthetic absorbable sutures treated in accordance with the principles of the present invention ranged from about 60 to 180% better than the controls. It is interesting to note that all of the four plasma surface treated PDS sutures produced in Examples 9 through 12 exhibited a statistically significant advantage over the corresponding untreated PDS sutures at the latter stage of hydrolytic degradation (i.e., at 28 and 42 days). Most of the plasma surface treated VICRYL sutures also showed better tensile strength retention than the controls, the range of improvement being from 20 to 80% better. In the DEXON sutures, the range of improvement on tensile breaking strength retention was considerably better than the controls. The results from plasma-treating MAXON sutures, however, were not as satisfactory as those obtained using the other synthetic absorbable sutures.

All the plasma-surface treated synthetic absorbable sutures exhibited higher hydrophobicity than the corresponding controls as evidenced in contact angle (0), specific wettability (SW), and work of adhesion (W) data. For example, both untreated PDS and MAXON sutures had a water contact angle of about 71 degrees, while the contact angle of all the treated PDS and MAXON sutures increased to 90 degrees and above. In addition, all the treated PDS and MAXON sutures showed negative SW, while the corresponding controls exhibited positive SW.

The creation of a more hydrophobic and/or a more cross-linked surface on the synthetic absorbable sutures by the plasma-surface treatments of the present invention improve the retention of tensile breaking strength of synthetic absorbable sutures. The increasing hydrophobic and/or cross-linked nature of the plasma-treated synthetic absorbable sutures resulted in a slower diffusion of chemicals into synthetic absorbable sutures as was evidenced in dye diffusion studies.

The hydrolytical degradation of synthetic absorbable sutures was examined by the change of their mass with time, i.e., weight loss. In general, except VICRYL sutures, all treatment conditions resulted in a faster weight loss upon hydrolysis, and the degree of accelerated weight loss depended on the types of synthetic absorbable sutures and plasma treatment conditions. For example, MAXON sutures, treated as described in Examples 13 and 14 exhibited twice the rate of weight loss as the control at 42 days, while most of plasma treated PDS sutures (Examples 13 and 14) showed about four times faster weight loss than the untreated PDS sutures at the same time interval. The accelerated weight loss in the plasma treated DEXON sutures, however, was not as profound as that observed in the monofilament MAXON and PDS sutures. This observed accelerated weight loss makes the plasma treated synthetic absorbable sutures quite attractive because the faster loss of suture mass after the suture becomes useless (i.e., no tensile strength left) could reduce the extent of undesirable chronic foreign-body reactions. It is very important to recognize, however, that this accelerated weight loss observed in plasma surface modified DEXON, PDS, and MAXON sutures was achieved not at the expense of accelerated tensile breaking strength loss.

It is also important to know whether the plasma surface treatments of the present invention adversely affect other properties important to sutures. One such property is stiffness which closely relates to the handling property and knot security/strength. Consequently, measurements were made of the bending stiffness of the synthetic absorbable sutures subjected to various plasma treatments as described in the Examples. In general, the plasma treatments used either slightly lowered the bending stiffness of synthetic absorbable sutures which is advantageous (e.g , the sutures produced in Examples 1 and 6) or showed no significantly statistical difference from the controls. PDS sutures, however, showed slight increases in bending stiffness due to a few plasma treatments such as in Example 12.

Because the plasma surface treatments of the present invention were limited to a thin layer, e.g., less than 1000Å, no apparent surface morphological changes due to treatments was observed, nor were any apparent surface morphological changes such as delamination, cracking, or crazing observed. Micrographs made of the hydrolyzed suture surface indicated less surface crack formation than the controls after 120 days in the bath.

The use of a surface cross-linking approach to modify materials has been recognized by some investigators to have a tendency to result in brittle materials which predisposes to mechanical failure due to surface fracture. Both stiffness and surface morphology data obtained and displayed above indicate that such concern is unfounded in the system of the present invention.

What is claimed is:

1. A method of treating a bioabsorbable synthetic polymer to modify the degradation rate thereof, said method comprising the step of:
modifying the hydrolyzation rate of said polymer by exposing said polymer to a gas plasma in a chamber at a pressure substantially below atmospheric for a sufficient time to increase the hydrophobicity or the cross-linking density or both the hydrophobicity and the cross-linking density of a surface layer thereof.

2. A method as defined in claim 1 wherein said exposure is for a time sufficient to increase said hydrophobicity or the cross-linking density or both the hydrophobicity and cross-linking density of said surface layer without substantially reducing the tensile strength of said polymer.

3. A method as defined in claim 1 wherein said time is sufficient to treat said layer to a depth between about 100 to 1500 Angstroms.

4. A method as defined in claim 1 wherein said time is sufficient to treat said layer to a depth between about between 200 and 1000 Angstroms.

5. A method as defined in claim 1 wherein said gas plasma is formed from a gas selected from the noble gases and gases containing silicon, carbon and/or fluorine moieties or a combination thereof.

6. A method as defined in claim 1 wherein said gas plasma is formed from a gas selected from the group consisting of argon, methane, trimethylsilane, tetrafluoroethylene and combinations thereof.

7. A method as defined in claim 1 wherein said plasma is formed between a pair of electrodes across which a radio frequency field is formed at the minimum power required to sustain said plasma.

8. A method as defined in claim 7 wherein said minimum power is between about 50 to 100 watts.

9. A method as defined in claim 7 wherein said time is between about 3 minutes to 60 minutes.

10. A method as defined in claim 1 including the steps of turning off said plasma and purging said chamber with a purge gas.

11. A method as defined in claim 1 wherein said polymer is selected from the group consisting of polyglycolic acids, polyglycolide-co-lactides, polylactic acids, polydioxanones, poly(glycolide-co-trimethylene carbonates), polyethylene carbonates, polyiminocarbonates, poly-$\beta$-hydroxybutyrates, polyester-amides, polyorthoesters, polyanhydrides, and cyanoacrylates.

12. An improved bioabsorbable synthetic polymer comprising:
a biosynthetic absorbable polymer the hydrolyzation rate of which has been modified by exposure of said polymer to a gas plasma in a chamber at a pressure substantially below atmospheric for a sufficient time to increase the hydrophobicity or the cross-linking density or both the hydrophobicity and cross-linking density of a surface layer thereof.

13. A polymer as defined in claim 12 and formed of a material selected from the group consisting of polyglycolic acids, polyglycolide-co-lactides, polylactic acids, polydioxanones, poly(glycolide-co-trimethylene carbonates), polyethylene carbonates, polyiminocarbonates, poly-$\beta$-hydroxybutyrates, polyester-amides, polyorthoesters, polyanhydrides, and cyanoacrylates.

14. A polymer as defined in claim 12 wherein said surface layer has been modified to comprise cross-linked hydrocarbons.

15. A polymer as defined in claim 12 wherein said surface layer has been modified to comprise a cross-linked structure similar to a perfluorinated hydrocarbon.

16. A polymer as defined in claim 12 wherein said surface layer has been modified to comprise a a Si-containing hydrocarbon surface.

* * * * *

UNITED STATES PATENT AND TRADEMARK OFFICE
CERTIFICATE OF CORRECTION

PATENT NO. : 5,236,563
DATED : August 17, 1993
INVENTOR(S) : Ih-Houng Loh

It is certified that error appears in the above-indentified patent and that said Letters Patent is hereby corrected as shown below:

On the title page, Item[75] Inventor, please delete "Inh" and substitute therefor -- Ih --.

Signed and Sealed this

Eighth Day of March, 1994

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,236,563
DATED : August 17, 1993
INVENTOR(S) : Ih-Houng Loh

It is certified that error appears in the above-indentified patent and that said Letters Patent is hereby corrected as shown below:

Column 1, line 3, insert "This invention was made with government support under grant number 1 R43 AR40454-01 awarded by the National Institutes of Health. The government has certain rights in the invention."

Signed and Sealed this

Thirteenth Day of December, 1994

Attest:

BRUCE LEHMAN

Attesting Officer     Commissioner of Patents and Trademarks